United States Patent [19]
Barker et al.

[11] 4,198,870
[45] Apr. 22, 1980

[54] CONSTANT POINT OF LOAD APPLICATION FRACTURE SPECIMEN LOADING MACHINE

[75] Inventors: Lynn M. Barker, Salt Lake City; Randall V. Guest, Bountiful, both of Utah

[73] Assignee: Terra Tek, Inc., Salt Lake City, Utah

[21] Appl. No.: 959,202

[22] Filed: Nov. 9, 1978

[51] Int. Cl.² ............................................. G01M 5/00
[52] U.S. Cl. ...................................... 73/799; 73/856
[58] Field of Search .................... 73/87, 799, 856, 807

[56] References Cited
U.S. PATENT DOCUMENTS

| | | | |
|---|---|---|---|
| 4,075,884 | 2/1978 | Barker | 73/807 |
| 4,075,886 | 2/1978 | Barker | 73/799 |
| 4,116,049 | 9/1978 | Barker | 73/87 |

Primary Examiner—Donald O. Woodiel
Attorney, Agent, or Firm—M. Reid Russell

[57] ABSTRACT

A constant point of load application fracture specimen loading machine for applying a load between grips that engage opposite grip groove faces of a slotted specimen that preferably has as a remainder portion in that slot a "V" shaped slot root whereby, when the machine grips are moved apart, they rotate so as to apply a constant point of load application to pull the specimen apart at that slot root. The machine of the present invention is useful for measuring the fracture toughness, fatigue-crack growth resistance, or stress corrosion crack growth resistance of slotted specimens providing a unique force application system whereby sliding friction losses are minimized, and other introduced effects, such as from specimen grip machining tolerances, or the like, are largely automatically compensated for.

20 Claims, 7 Drawing Figures

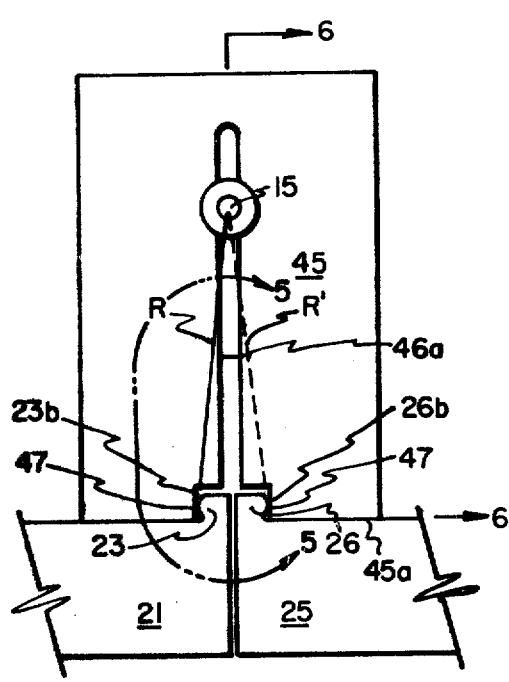
FIG. 4
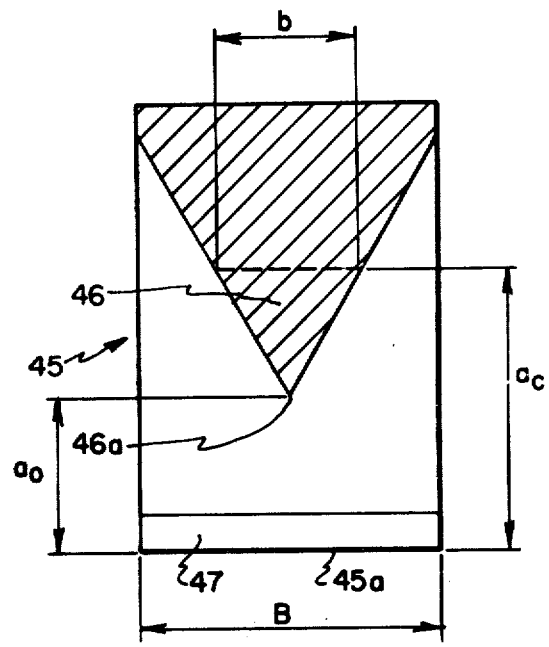
FIG. 6
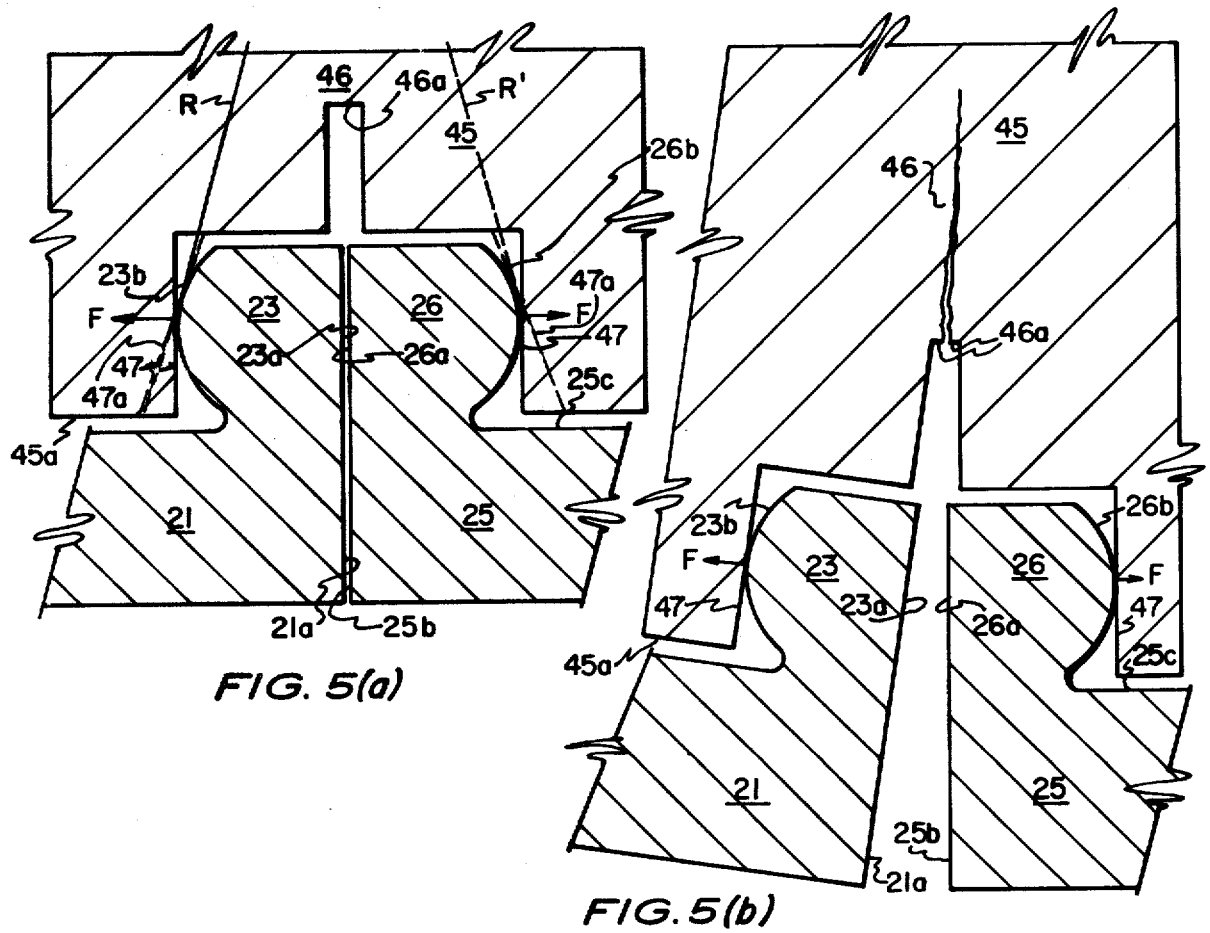
FIG. 5(a)
FIG. 5(b)

CONSTANT POINT OF LOAD APPLICATION FRACTURE SPECIMEN LOADING MACHINE

DESCRIPTION OF THE INVENTION

1. Field of the Invention

This invention relates to the discipline of fracture mechanics in which the resistance offered by materials to crack growth, known as fracture toughness, is of prime concern.

2. Prior Art

The testing of materials for fracture toughness, fatigue crack growth resistance, and stress corrosion crack growth resistance is most often done with specimens containing a machined slot in which crack growth initiates from the root of the slot. Such tests all involve an appropriate specimen loading sequence, where the loading applied to the specimen tends to increase the machined slot width.

Materials testing machines capable of providing such loading have long been known and are in common use. Such machines often involve arms that affix to parts of such specimen and, when energized, move apart, widening the specimen slot. The arrangement whereby such a testing machine is locked to the specimen must be chosen such that friction is minimized, and such that the point of application of the load does not change during the test. These considerations are set forth in the ASTM E 399-74, "Standard Method of Test for Plane-Strain Fracture Toughness of Metallic Materials," for example. In the method of this standard, the load point is fixed in a compact toughness specimen by inserting pins through two holes in the specimen, the pins being essentially the same diameter as the holes. The load is then applied by pulling on the ends of the pins with clevises attached to the loading machine. Friction is minimized by using specially-made clevises with flats machined in the holes through which the loading pins fit, such that the pins can roll slightly during the test, rather than being forced to slip due to the rotation which occurs in the specimen arms as it is loaded.

Of recent times, fracture toughness testing has been undertaken on short rod specimens. An example of one such specimen is shown in U.S. Pat. Nos. 4,075,884 and 4,116,049, which patents one of the co-inventors hereto was the inventor of. A machine shown in U.S. Pat. No. 4,116,049 teaches one arrangement for loading of such specimen that, like other heretofore known testing machines, involves grips for fitting into grip grooves machined into the face of the specimen such that the specimen mouth can be pulled open via the grips. However, in earlier machines, unlike the present invention, when the grips thereof are moved apart, they travel along a straight line such that the exact location of the load point in the specimen grip grooves can change during the test due to the slight rotation of the front of the specimen as it is flexed open or because of plastic deformation of the specimen at the point of contact with the grips, or both. Furthermore, friction, that is detrimental to the test results, can also be present in such earlier machines because of the rotation of the mouth of the specimen relative to the grips when the grips, during the test, remain aligned along the pulling axis of the testing machine.

The present invention solves the above problems of prior test machines by providing a grip loading system for short rod and similar fracture toughness specimens, arranged to:

minimize friction during a test;

provide that the point of application of the load on the specimen tends to remain fixed during a test, even in the presence of the flexing open of the specimen mouth and plastic deformation of the specimen grip grooves at the point of contact with the grips;

provide that any deviation in load point that may occur due to certain specimen machining tolerances or due to the flexing of the specimen during the test will be automatically compensated for by the loading system such that a resulting error in measured data is minimized; and provide that any deviation in load point application on the specimen that might occur because of plastic deformation of the specimen grip groove is minimized by the use of crowned grip faces.

Within the knowledge of the inventors, there has not heretofore existed a machine like that of the present invention involving a rotation of machine grips to conform to specimen opening during a test so as to maintain nearly constant points of load application to the specimen and, therefore, the present invention is believed to be both novel and unique and a significant improvement in the art.

SUMMARY OF THE INVENTION

It is a principal object of the present invention to provide a constant point of load application fracture specimen loading machine for performing fracture toughness testing on both brittle and ductile specimens.

Another object is to provide a machine for testing short rod and short bar specimens capable of altering the orientation of the loading grips thereof as slotted specimen halves are split apart so as to maintain nearly constant points of load application thereto.

Another object is to provide a machine having grips whose surfaces are arranged for contact with grip grooves formed in a specimen face and oriented during the test to minimize friction losses between the grips and grip groove surfaces.

Still another object is to provide a machine whose operation automatically compensates for errors and other effects introduced by machining inconsistancies and variations from optimum tolerances, and by flexing of the specimen during testing.

Principal features of the present invention in a constant point of load application fracture specimen loading machine preferably include fixed rigid outer arms preferably mounted to a table with a rigid center arm pivotally connected thereto proximate to the ends thereof. Each arm is arranged to mount a grip coupled thereto appropriately below the pivot; such that when the arms are moved together, the grips face oppositely. Each grip has a cantilever face, the faces to engage the faces of the grip grooves in a short rod, short bar or other fracture test specimen. The grips are arranged such that, when the arms are pivoted apart, the oppositely facing grips will travel therewith moving in an arc that closely conforms to the arc made by the slotted specimen grip groove faces as they split apart.

The outside arms are preferably secured to act together as a single lever; the pivot serving as a fulcrum with the center arm serving also as a lever. The force applied to the specimen is therefore related to the measured force applied at the end of the center arm and to the ratio L/R, where L is the distance from the pivot point to where force is applied at the end of the center arm, and R is the distance from the pivot point to where the grip cantilever faces contact the specimen grip grooves. Additionally, where a test specimen may be located correctly with respect to the pivot, the distance R could still be non-ideal due to machining tolerances of the specimen grip grooves, or the like, with the point of load application within the specimen grip grooves then also being non-ideal, resulting in a variance in the load required to fracture the specimen. The present invention is arranged such that the change in the load required to fracture the specimen and the error in calculating the load applied to the specimen due to the variance in R will be nearly equal in magnitude but opposite in direction, thus nearly cancelling each other.

To limit load point changes associated with elastic and/or plastic deformation of the grips or the grip grooves, the grip cantilever faces that engage the grip grooves in the specimen are designed to be arched or rounded appropriately to be symmetric around the initial load point. The present invention also provides a load applying system that minimizes sliding friction losses eliminating thereby the need to make allowances for friction losses and the like.

The present invention preferably also includes arrangements for rotating the outside and center arms with respect to each other around a pivot, an arrangement for measuring the moment force applied around the pivot, and an arrangement for indicating the opening across the specimen halves at the load points as the specimen splits apart.

Further objects and features of the present invention will become more apparent from the following detailed description, taken together with the accompanying drawings.

THE DRAWINGS

FIG. 1, is a profile perspective view taken from the front and off to one side of a first embodiment of a constant point of load application fracture specimen loading machine of the present invention;

FIG. 2, a view like that of FIG. 1, only showing the center arm and grip thereof pivoted with respect to stationary outer arms and grip showing portions of an outside and the center arms broken away to expose the grips attached thereto;

FIG. 3, an exploded view of the constant point of load application fracture specimen loading machine of FIG. 1;

FIG. 4, an expanded cross sectional view of the grips secured to the outer and center arms as shown in FIG. 1, a slotted specimen shown mounted thereto, showing, in solid and broken lines labeled R and R' respectively, the moment arms from the pivot to the point of load application of grip cantilever faces on specimen grip grooves of optimum and other than optimum points of load application;

FIG. 5(a), an expanded sectional view taken within the lines 5—5 of FIG. 4, showing the grip cantilever faces in contact with faces of grip grooves formed in the specimen;

FIG. 5(b), a view like that of FIG. 5(a) showing the grips moved apart and the specimen fractured; and FIG. 6, a sectional view of the specimen removed from the machine taken across the slot root and rotated to a top plan view taken along the lines 6—6 of FIG. 4, with letters identifying the different dimensions of the specimen.

DETAILED DESCRIPTION

Figures 1, 2:
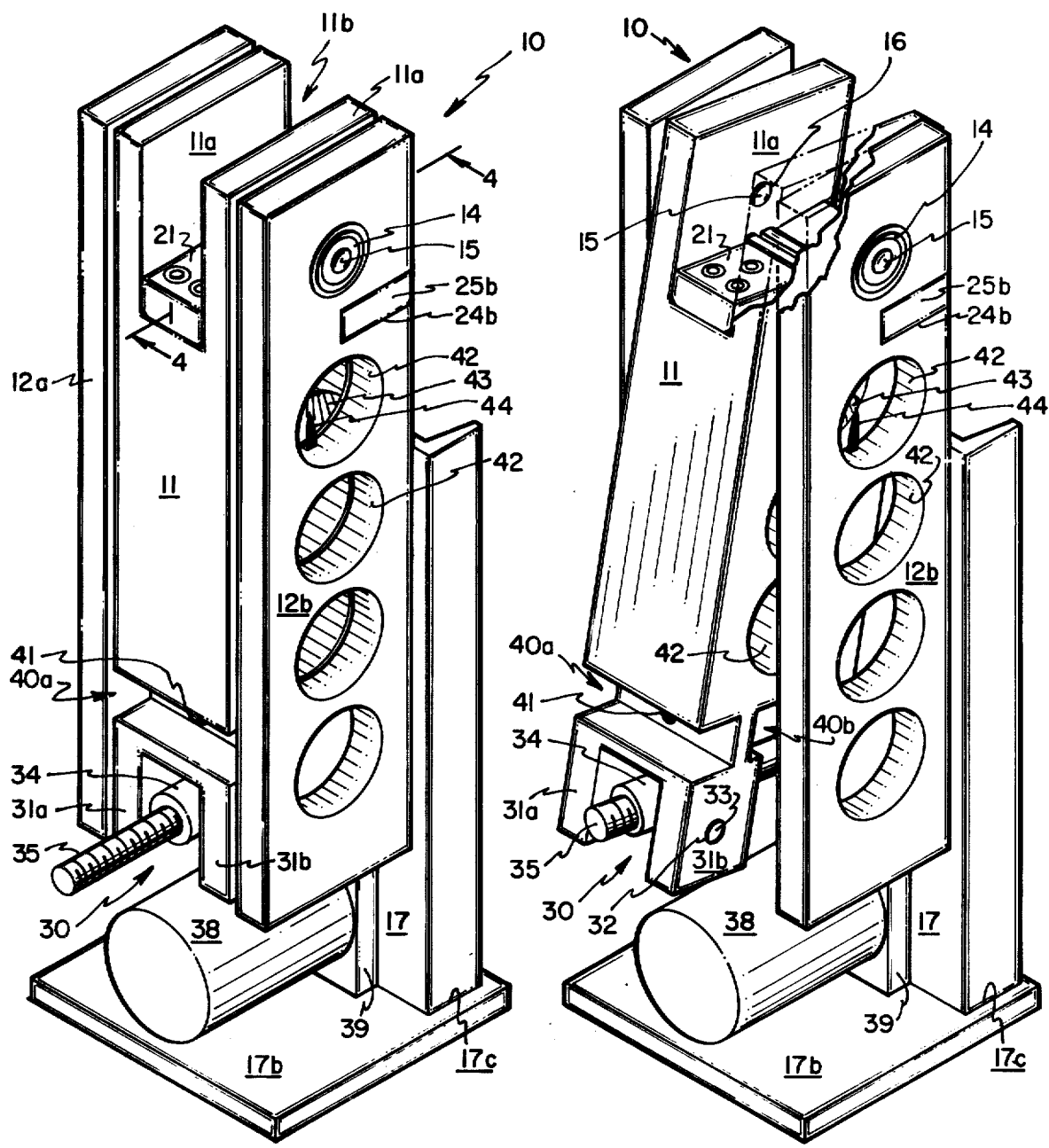
Figure 3:
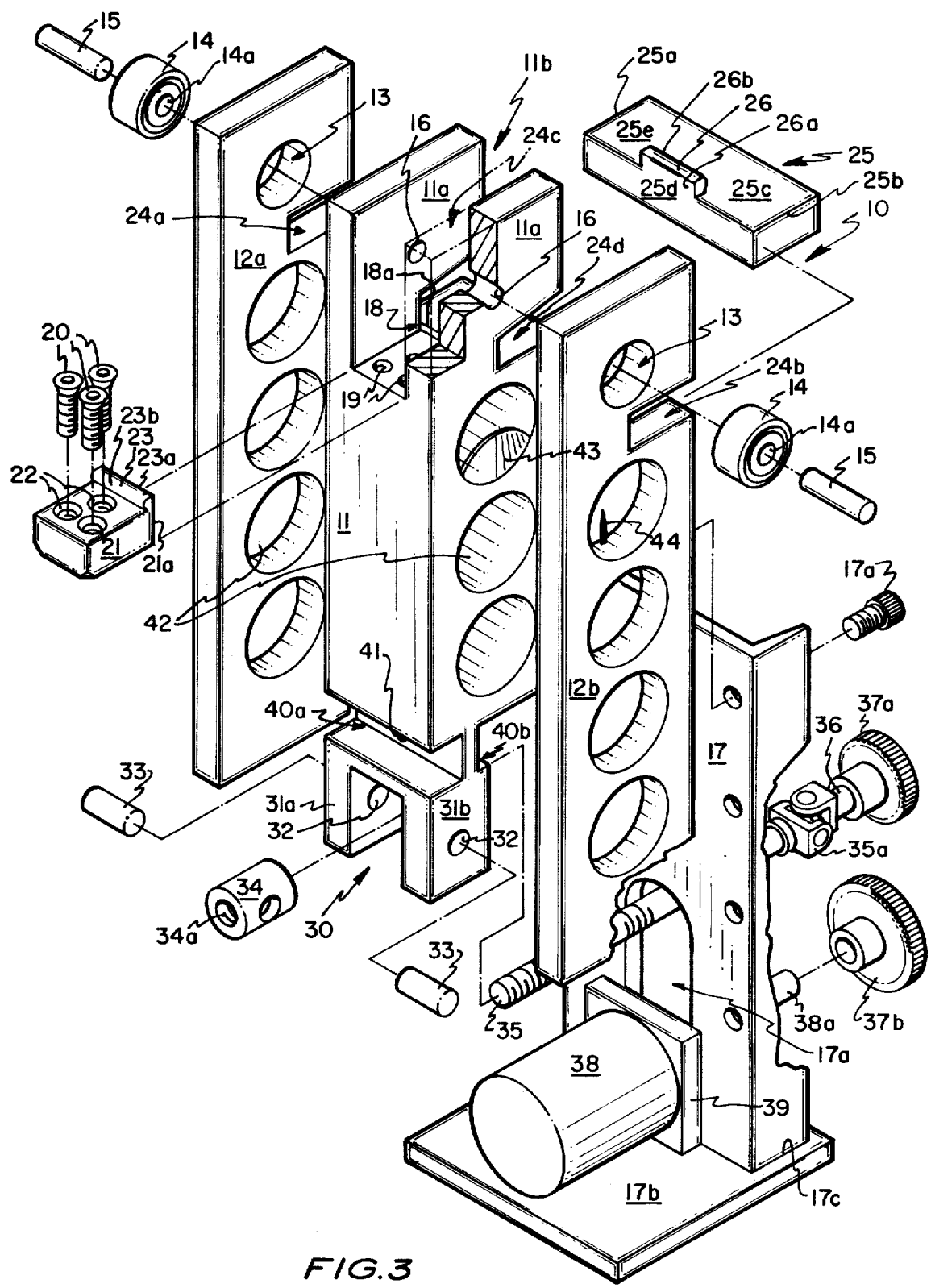

Referring now to the drawings:

FIGS. 1 through 3 show a preferred embodiment of a constant point of load application specimen loading machine 10 of the present invention hereinafter referred to as "machine." Shown therein, machine 10 preferably consists of a center arm 11 and two outside arms 12a and 12b. The exploded view of FIG. 3 shows holes 13 formed through the outside arm 12a and 12b ends, receiving bearings 14 therethrough that are preferably roller bearings or like friction minimizing devices. Through openings 14a in bearings 14, pivots 15 are installed, which pivots are secured in holes 16 formed in sides 11a of a notched end portion 11b of center arm 11. So arranged, the center arm 11 is pivotally connected to the outside arms 12a and 12b at pivots 15, and the outside arms, as shown in FIG. 3, are secured along the sides to a channel base 17, preferably by screws 17a. The channel base 17 is, in turn, secured at its bottom end 17c to extend upwardly and at a normal angle from a table 17b, or like stationary platform, such that the center arm 11 swings between the outside arms.

Within the notched end portion 11b of center arm 11, across the web between sides 11a, as shown best in FIG. 3, a step 18 is arranged having a front wall 18a therewith. The bottom of step 18 adjacent to front wall 18a has appropriate holes 19 formed therein for receiving screws 20, or like fasteners. A grip base 21 is formed to fit within that step 18 that has holes 22 formed therethrough that align with holes 19, with the screws 20 turned therethrough to secure together the grip base 21 within step 18. Arranged on grip base 21 across a top leading edge of face 21a thereof that butts against step from wall 18a thereof is arranged a grip 23 that preferably has an arched or rounded cantilever face 23b, hereinafter referred to as "face," formed on a rear face with a flat face 23a formed in the opposite leading face thereof.

Referring to FIG. 3, lateral notches 24a and 24b are formed across portions of outside arms 12a and 12b extending therein a distance sufficient for receiving and securing end portions 25a and 25b of a stationary grip base 25, which end portions 25a and 25b are also arranged to slide freely within grooves 24c and 24d formed in sides 11a of center arm 11. Arranged on a top face 25c of stationary grip base 25, so as to fit within sides 11a of center arm 11, is a grip 26 that extends outwardly in the plane of a grip base leading face 25d. So arranged, a grip forward flat face 26a of grip 26 will close together with the flat forward face 23a of grip 21 when center arm 11 is rotated to a relaxed position and has an arched or rounded cantilever face 26b, hereinafter referred to as "face." As will be described in detail later herein, with grip grooves of a slotted specimen installed over grips 23 and 26, a pivotal movement of center arm 11, as shown in FIG. 2, will move those grips apart, forcing apart also the specimen across its slot opening until fracture occurs at an apex of a root of the slot formed in the specimen.

Center arm 11, at its end opposite to notch 11b has a yoke 30 formed therewith at parallel sides 31a and 31b. Each center arm side 31a and 31b has a hole 32 formed therethrough, which holes receive pins 33 journaled therethrough to pivotally maintain a sleeve 34. Shown best in FIG. 1 and 2, a screw 35 is turned in threads formed longitudinally in a center opening 34a through sleeve 34, the turning of said screw to move the sleeve 34 and connected arm 11 appropriately as between the attitudes shown in FIGS. 1 and 2. A preferred arrangement to so turn the screw 35, as shown best in the exploded view of FIG. 3, consists of a driver gear 37b, that is connected by a shaft 38a that is turned by motor 38. The driver gear 37b meshes with, to turn, a driven gear 37a that is second to a shaft 36. Shaft 36 connects to one side of a universal joint 35a with the other side thereof secured to an unthreaded end of screw 35. Shafts 36 and 38a pass through a notch 17a formed in channel base 17, with the motor 38, preferably secured to a collar 39, that is connected by appropriate fasteners, not shown, to the channel base 17, extending across notch 17a.

By turning the threaded end of screw 35 appropriately, the sleeve 34 will be moved appropriately, the center arm 11 traveling therewith. As shown in FIG. 2, movement of center arm 11 with respect to outside arms 12a and 12b will spread apart grips 23 and 26. While the described screw 36 and the arrangement for turning it as described with respect to FIGS. 1 through 3, is preferred, it should be understood that any conventional apparatus or assembly for similarly moving center arm 11 with respect to outside arms 12a and 12b could be so used without departing from the subject matter coming within the scope of this disclosure. Further, though the outside arms 12a and 12b are shown to be fixed to channel base 17 that is in turn fixed to table 17b, the outside arms could themselves be fixed to a table.

Depending upon the apparatus employed, as described, to move center arm 11 with respect to outside arms 12a and 12b, it may be possible to measure the force exerted in moving that center arm at the source of that movement. However, for measuring the force applied to center arm 11, the present invention preferably employs strain gages 41 that are shown installed within notches 40a and 40b formed in center arm 11. So arranged, when center arm 11 is moved outwardly, as shown in FIG. 2, a compressive stress is exerted on the face of notch 40a and a tensile stress is exerted across the face of notch 40b. A strain gage 41 installed in forward notch 40a should therefore be one arranged for sensing compressive stresses and the strain gage 41 installed in rearward notch 40b should be one arranged to measure tensile stresses. The compressive and tensile stresses so measured by strain gages 41 can then be correlated to determine the force applied on the center arm 11, which measurement, as will be shown later herein, is then used to compute the specimen fracture toughness.

In FIGS. 1 through 3, the respective outside arms 12a and 12b, as well as center arm 11, are shown as having holes 42 formed therethrough. The purpose of these holes is for limiting heat transfer through the members such as when the device is used in tests performed under controlled temperature conditions. Further, it is desirable to provide the present invention with an arrangement for measuring, as it occurs, the opening between grip contact points with specimen grip grooves as the specimen is split apart under load. To provide such arrangement for measuring that opening, as shown in FIGS. 1 through 3, the present invention preferably includes a scale 43 within a hole 42 in the center arm 11, adjacent to this scale, and arranged alongside thereto within a hole 42 formed in outside arm 12b is a pointer 44. The scale 43 is calibrated with respect to the distance therefrom to the pivot 15 and the distance from the pivot 15 to where grip faces 23b and 26b optimumly engage the grip groove surfaces of a specimen. So arranged, by aligning pointer 44 appropriately, the distance between the grip groove engaging grip faces 23b and 26b, at various points in the loading cycle, can be directly read from the scale. Other arrangements for measuring the distance between the grip faces 23b and 26b during specimen opening should be understood to be appropriate for incorporation in lieu of scale 45 and pointer 44 without departing from the scope of this disclosure. Such could involve a displacement transducer arranged between the arms, not shown; an arrangement for measuring the screw turns of screw 36 as it is turned in sleeve hole 34a, not shown; a caliper device for arrangement with the grips themselves for physically measuring the distance between the grip faces, not shown, or the opening in the specimen slot could be measured.

In FIG. 4 is shown a sectional view taken along the line 4—4 of FIG. 1 only including a slotted short rod specimen 45 mounted to grips 23 and 26 and including the pivot 15 that acts as a fulcrum for outside and center arms 12a, 12b and 11 that, as lever arms, apply a load to the specimen 45. The specimen 45 could, of course, be a short bar specimen, and is slotted, as shown in cross-section in FIG. 6, to leave as a remainder portion a "V" shaped root 46 having an apex 46a. Specimen 45 preferably has grip grooves 47 formed therein across a slotted face 45a that accommodate grip faces 23b and 26b, respectively, of grips 23 and 26.

While grip grooves 47 are preferably arranged parallel to the specimen axis, as shown in FIGS. 4, 5(a) and 5(b), they could, of course, be slightly non-parallel due to machining tolerances, as shown by the broken line representations 47a in FIG. 5(a). The application of a loading force F to a specimen 45 shown in FIGS. 5(a) and 5(b), at an optimum point of application in grip grooves 47, is shown schematically in FIG. 4 and FIG. 5(a) as a moment arm R that extends from pivot 15 to that optimum point of contact of grip faces 23b and 26b in grip grooves 47. A broken line R' shows that moment arm when the point of contact of the grip faces 23b and 26b within the grip grooves 47 is other than the optimum, that point of contact having been rotated upwardly around the circumference of grip faces 23b and 26b in the grip grooves 47a. Such other than optimum location of the grip faces in the grip grooves may occur should the grip grooves 47 be slanted, as shown at 47a, or the like, in the manufacture thereof. The effect of changing the point of load application to the specimen 45 from an optimum will be described in detail later herein with respect to an alteration in the peak load required to fracture the specimen.

FIG. 5(a), of course, shows an enlarged view of the grips 23 and 26 arranged within the grip grooves 47 in the slotted specimen 45 prior to specimen loading. FIG. 5(b) is a view like that of FIG. 5(a), only does not show non-optimum grip grooves 47a and R and R', and shows the grip 23 on center arm 11 as having been moved apart from grip 26, the specimen fracturing at the root 46 from the apex 46a thereof during the loading of the specimen.

Shown in FIG. 5(b), grip 26, as detailed earlier herein, is preferably stationary with grip 23, secured to center arm 11, rotated apart therefrom. Obviously, as the center arm 11 only is rotated, specimen 45 will be canted somewhat during a test, as shown in FIG. 5(b).

The applied forces, however, that are shown as arrows F in FIGS. 5(a) and 5(b), will be continuously applied at nearly the same point on the grip grooves, with the arc opening between the grip faces 23b and 26b conforming approximately to the specimen slot arc opening. The orientation of the grip faces of the present invention thereby changes, during a test, in conformity to specimen deformation. Other forces, such as static friction forces, that maintain the grip faces in grip grooves are present, but such forces can be ignored in computing fracture toughness. The arc of rotation of center arm 11 at the peak or maximum load applied to the specimen 45 is therefore equal or nearly equal to the arc of curvature made by the specimen halves as the specimen is split apart. Of course, the arc of rotation of center arm 11 is dependent upon a proper selection of the location of the pivot 15 with respect to the particular specimen being tested, and so a change in specimen geometry may necessitate a change in the location of pivot 15.

In most prior short rod and short bar specimen grip loading machines, the grip portions thereof act on a specimen in only a straight line, the loading points on the specimen halves therefore changing during that test because of rotation of the specimen halves as it is flexed open, thus producing an unaccounted for change in the load necessary to fracture the specimen. Such can also create sliding friction that can adversely affect the measurement of the fracture toughness. The present invention, by altering the orientation of the grips during the test, corrects these problems. Also, the present invention, by providing arched or rounded grip faces 23b and 26b, provides for a more nearly fixed point of application of load to the specimen grip grooves, even if plastic deformation occurs, the grip faces indenting the specimen grip groove faces symmetrically around the contact points.

While it would be optimum to be able to provide specimen grip grooves 47 that are consistantly the same, because of potential differences in manufacture, i.e., where the slant of that grip groove may not be normal to the specimen face, or the like, problems with a constant positioning of the contact point between the specimen grip grooves and the grip faces 23b and 26b may occur. In FIG. 5(a), the moment arm from the pivot 15 to the point of contact of grip faces 23b and 26b is shown to have moved up within the non-optimum grip grooves 47a, from R, the optimum, to a different moment arm R' that is shown in broken lines. Obviously, an alteration in the length of the moment arm wherethrough a load is applied will produce errors in the computation of the load required to fracture the specimen. Also, the required load to fracture the specimen will change as a result of a different contact point within the grip groove. In a test performed by the machine 10 of the present invention, these effects are, however, offsetting, as shown hereinbelow, and so will not materially affect the test results.

Assuming that there is a change from the optimum grip face to grip groove points of contact, shown as moment arm R, the distance between the center of rotation of pivot 15 to the contact point between the grip face and the specimen grip groove would be changed from that optimum to a moment arm R'. The mechanical advantage of the load applied through pivot 15 by moving center arm 11 would thereby be increased by a shortening of the distance from the fulcrum to the load. With R the normal distance or moment arm from that fulcrum or pivot 15 to the point of the load application to the specimen; letting L be the distance from the fulcrum to the point of application of the external load that separates the outer and center arms 12a, 12b and 11, respectively; F the external applied load and P the load felt on the specimen 45, then L/R is the mechanical advantage, and P=(L/R)F. A change in load P due to a small change in R would therefore be:

$$dP_1 = -\frac{L}{R} F\left(\frac{dR}{R}\right) \tag{1}$$

or $$\frac{dP_1}{P} = -\frac{dR}{R} \tag{2}$$

Just as a change in the distance from the fulcrum to the load point on the specimen alters the loading force applied to the specimen, such change in force application point also alters the load, P, required to advance the crack from apex 46a through a critical location in the slot root 46, which distance is labeled $a_c$ in FIG. 6. Therefore, as the equation for specimen fracture toughness (the critical plane strain stress intensity factor, $K_{Ic}$) is based on a particular assumed load point, there will be a change in the actual load at the specimen if there is a change in that load point. The magnitude of such change can be measured by experiment, or can be estimated mathematically. Hereinbelow are arranged formulas for determining or deriving the change in load affected by such alteration in the load point.

For the computations hereinbelow, reference is hereby made to FIG. 6, wherein are labeled the various specimen dimensions and distances for a slotted specimen 45 having as a remainder portion a "V"-shaped root 46, hereinafter referred to as slot root. Experimentally, the variation in the peak load in a test has been measured as a function of "$a_o$," the distance from the point of load application to the apex 46a of the slot root 46, where the point of load application on the specimen was held constant. It is to be expected that a variation in that load point would have approximately the same magnitude effect on the peak load as an equal variation in "$a_o$." Assuming this to be the case, and letting small "y" be the distance from the specimen face to the load point, then, $$\frac{dP_2}{dy} = \frac{-dP_2}{da_o} \tag{3}$$

where "$dP_2$" represents a change in "P" resulting from a change in load point, "dy." With "B" equaling specimen diameter, experiments have shown that, $$\frac{B}{P} \frac{dP_2}{da_o} = -1 \pm 0.3 \tag{4}$$

Therefore, we have, from combining the above equations, $$\frac{B}{P} \frac{dP_2}{dy} \cong +1. \tag{5}$$

Then, since "dy" is very nearly equal to "−dR", then the above would be:

$$\frac{B}{P} \frac{dP_2}{dR} \cong -1, \tag{6}$$

or

-continued
$$\frac{dP_2}{P} \simeq \frac{dR}{B}$$

Preferably, the machine 10 is designed such that "R" is approximately equal to "B." Therefore, comparing the above equations (2) and (6), we see that the two load changes "dP₁" and "dP₂" differ in magnitude by only a few percent. Further, they are cancelling effects: a negative "dR" (a shortening of R to R') produces a larger load on the specimen than would be calculated from the externally applied load, but results in the need for a larger load to be applied to fracture the specimen when the load is moved inwardly from the specimen face.

In the above, the variation in "P" as a function of the load point was estimated from experiments on the effects of a variation in "$a_o$." It is also possible to calculate the effect of the load point variation on "P." Such calculations lead to the same conclusion, namely, that the effects of the change in load necessary to fracture the specimen and the error in calculating the load applied to the specimen are nearly self-cancelling provided that "R" is approximately equal to "B."

The calculated peak load "Pmax"=(L/R) $F_{max}$ at the time of specimen fracture can therefore be used for determining the critical stress intensity factor for short rod and short bar specimens, without making allowance for errors produced by a variation from an optimum of the contact points of the grips in specimen grip grooves.

As outlined hereinabove, the machine 10 is unique in that it provides for a consistant point of load application to the specimen, altering the orientation of the grips to conform to or allow for specimen opening across its slot during loading. Sliding friction is thereby minimized to a point where it need not be considered in calculating specimen fracture toughness. The only force that need be considered in computing specimen fracture toughness therefore is the applied load. Static friction forces that hold the grip faces in the grip grooves are not sensed in such tests as a force inducing specimen fracture.

Operation, as described, of the above-described machine 10 of the present invention makes possible a simplified method for measuring fracture toughness of a short rod or bar specimen 45. Similar to earlier methods, and as detailed in the prior U.S. Patent of inventor Lynn Barker hereof, the present invention also includes the steps of: forming a short rod specimen, from a material, slotting logitudinally that specimen to leave a V-shaped root 46, or like shape, as a remainder, and fitting that specimen over grips of a machine that will move apart, loading the specimen across the slot until fracture occurs. As with other former methods, the present invention provides for measurement of the peak or maximum load exerted on the specimen whereat fracture occurs. A unique step performed by the present invention, however, as detailed hereinabove, is the constant reorientation of the grips during the test to provide a nearly fixed point of load application to the specimen, avoiding doing unrecoverable work against friction at the grip faces.

Although a preferred embodiment of our invention in a fracture specimen loading machine has been herein disclosed, it should be understood that the present disclosure is made by way of example and that variations are possible without departure from the subject matter contained herein. Further, while certain arrangements for measuring peak load and for measuring the opening across the specimen slot have been shown and described herein, such arrangements are made by way of example, and other apparatus appropriate to performing the described functions could be substituted therefore without departing from the subject matter coming within the scope of the present disclosure. Also, while a preferred embodiment of the present invention as involving fixed outside arms 12a and 12b, with center arm 11 being free to pivot with respect thereto is shown, alternatively, both outer and inner arms could both be arranged to pivot with respect to one another, or the pivot could be arranged to connect ends of dog legs each extending from a single arm, each single arm mounting a grip and operating, as described. Or other configuration of lever arms and grips therewith could be so arranged, without departing from the subject matter coming within the scope of this disclosure. Therefore, the present invention should be understood to not be limited to the particular arrangement of pivotally connected outside and center arms or levers as disclosed herein. Rather, any arrangement of a pivot spaced above grips secured to arms or levers functioning as described herein should be understood to fall within the scope of this disclosure.

The present disclosure should be understood to be made by way of example and variations are possible without departing from the subject matter coming within the scope of the following claims, which claims we regard as our invention.

We claim:

1. A constant point of load application fracture specimen loading machine consisting of,
    a plurality of lever arms;
    means for pivotally connecting together said lever arms;
    a pair of grips each secured to a lever arm below said pivot means, which grips, when said lever arms are pivoted together, fit within grip grooves of a test specimen, which grips, when said lever arms are pivoted apart, are moved therewithin in an arc that approximates an arc of travel that is made by segments of said test specimen as it splits apart;
    means for pivoting apart said lever arms; and
    means for measuring the load applied to said test specimen through the lever arms.

2. A machine as recited in claim 1, wherein the plurality of lever arms consists of,
    two outside arms with a center arm sandwiched therebetween, said outside and center arms pivotally connected together proximate to ends thereof.

3. A machine as recited in claim 1, further including,
    means for fixing in place one of said lever arms with the means for pivoting apart of said lever arms arranged to act on the other lever arm.

4. A machine as recited in claim 1, wherein the means for pivotally connecting together said lever arms consists of,
    bearing means secured in one lever arm; and
    a shaft secure to the other lever arm and appropriately fitted to said bearing means.

5. A machine as recited in claim 1, wherein
    crown means are secured to the faces of the grips that engage the specimen grip grooves for assuring that the center of load application does not change location during a test due to specimen grip engaging surface and grip deformation.

6. A machine as recited in claim 5 wherein the crown means consists of, arched grip faces.

7. A machine as recited in claim 1, wherein the means for pivoting apart said lever arms consists of,
   a threaded collar;
   means for securing one of the lever arms across said collar;
   means for fixing in place the other lever arm;
   screw means turned in said threaded collar; and
   means for turning said screw means for moving appropriately said threaded collar and connected lever arm.

8. A machine as recited in claim 7, wherein
   the threaded collar is pivotally secured to the lever arm; and,
   the means for turning said screw means consists of,
   a motor having an output shaft turned thereby;
   a driver gear secured to the end of said output shaft;
   a driven gear intermeshing with said driver gear;
   a shaft secured to said driven gear and extending therefrom; and,
   a universal joint secured across said shaft opposite to said driven gear, which universal joint connects also to said screw means.

9. A machine as recited in claim 1, wherein the means for measuring the applied load consists of,
   strain gage means secured to the lever arm for sensing flexure thereof; and
   means connected to said strain gage means for recording load forces applied thereto.

10. A machine as recited in claim 1, further including means for measuring the opening between the points on the grip faces that engage the specimen grip groove surfaces.

11. A machine as recited in claim 10, wherein
    the means for measuring grip face opening consist of,
    a pointer arranged with one lever arm; and
    an appropriately marked scale arranged with the other lever arm such that, when said lever arms are pivoted apart said pointer will align with an appropriate marking on said scale reflective of the opening between the points on the grip faces that engage the specimen grip groove surfaces.

12. A constant point of load application fracture specimen loading machine consisting of,
    a lever arm;
    a fixed base;
    means for pivotally connecting together said lever arm and fixed base;
    a pair of grips, one each, secured to said lever arm and fixed base below said pivot means, which grips, when said lever arm is pivoted together with said fixed base, fit within grip grooves of a test specimen, and when said lever arm is pivoted apart from said fixed base, the grip secured thereto is moved in an arc that approximates an arc of travel that is made by segments of said test specimen as it splits apart;
    means for pivoting apart said lever arm from said fixed base; and
    means for measuring the load applied to said test specimen through the lever arm.

13. A machine as recited in claim 12, wherein the means for pivotally connecting together said lever arm and fixed base consists of,
    bearing means secured in said lever arm; and
    a shaft source to said fixed base and appropriately fitted to said bearing arm.

14. A machine as recited in claim 12, wherein
    crown means are secured to the faces of the grips that engage the specimen grip grooves for assuring that the center of load application does not change location during a test due to specimen grip engaging surface and grip deformation.

15. A machine as recited in claim 14, wherein the crown means consists of,
    arched grip faces.

16. A machine as recited in claim 12, wherein the means for pivoting apart said lever arm from said fixed base consists of,
    a threaded collar;
    means for securing said lever arm across said collar;
    screw means turned in said threaded collar; and
    means for turning said screw means for moving appropriately said threaded collar and connected lever arm.

17. A machine as recited in claim 16, wherein
    the threaded collar is pivotally secured to the lever arm; and,
    the means for turning said screw means consists of,
    a motor having an output shaft turned thereby;
    a driver gear secured to the end of said output shaft;
    a driven gear intermeshing with said driver gear;
    a shaft secured to said driven gear and extending therefrom; and,
    a universal joint secured across said shaft opposite to said driven gear, which universal joint connects also to said screw means.

18. A machine as recited in claim 12, wherein the means for measuring the applied load consists of,
    strain gage means secured to the lever arm for sensing flexure thereof; and
    means connected to said strain gage means for recording load forces applied thereto.

19. A machine as recited in claim 12, further including
    means for measuring the opening between the points on the grip faces that engage the specimen grip groove surfaces.

20. A machine as recited in claim 19, wherein
    the means for measuring grip face opening consist of,
    a pointer arranged with the lever arm; and
    an appropriately marked scale arranged with the fixed base such that, when the said lever arm is pivoted apart from said fixed base said pointer will align with an appropriate marking on said scale reflective of the opening between the points on the grip faces that engage the specimen grip groove surfaces.

* * * * *